(12) United States Patent
Anderson et al.

(10) Patent No.: US 6,689,383 B1
(45) Date of Patent: Feb. 10, 2004

(54) CHROMIUM-HISTIDINE COMPLEXES AS NUTRIENT SUPPLEMENTS

(75) Inventors: Richard A. Anderson, Bowie, MD (US); Marilyn M. Polansky, Beltsville, MD (US); Noella A. Bryden, Ellicott City, MD (US)

(73) Assignee: The United States of America as represented by the Secretary of Agriculture, Washington, D.C.

( * ) Notice: Subject to any disclaimer, the term of this patent is extended or adjusted under 35 U.S.C. 154(b) by 339 days.

(21) Appl. No.: 09/414,645

(22) Filed: Oct. 8, 1999

(51) Int. Cl.[7] ................................. A61K 9/20
(52) U.S. Cl. ................ 424/464; 424/451; 424/439; 424/442; 424/400; 556/57
(58) Field of Search ................ 556/57; 424/442, 424/464, 400, 451

(56) References Cited

U.S. PATENT DOCUMENTS

| | | | |
|---|---|---|---|
| 3,925,433 A | 12/1975 | Abdel-Monem et al. | 260/438.5 R |
| 4,167,564 A | * 9/1979 | Jensen | 424/177 |
| 4,830,716 A | 5/1989 | Ashmead | 204/72 |
| 4,863,898 A | 9/1989 | Ashmead et al. | 514/6 |
| 5,614,553 A | 3/1997 | Ashmead et al. | 514/505 |
| 5,702,718 A | 12/1997 | Ridenour | 424/438 |

OTHER PUBLICATIONS

Anderson et al. 1996. Journal of Trace Elements in Experimental Medicine, vol. 9, pp. 11–25.

* cited by examiner

*Primary Examiner*—Thurman K. Page
*Assistant Examiner*—Liliana Di Nola-Baron
(74) *Attorney, Agent, or Firm*—John D. Fado; Janelle S. Graeter

(57) ABSTRACT

Chromium is an essential element which has been shown to have beneficial effects on carbohydrate and lipid metabolism. Often, dietary intake is suboptimal, and nutritional supplements may not be effective due to poor absorption in the gastrointestinal tract. A novel chromium-histidine complex has been prepared which significantly improves absorption capability over current available chromium nutritional supplements. The complex is safe, easily prepared and may be combined with an ingestible carrier for consumption as a tablet, capsule, aqueous solution, food or food product.

5 Claims, No Drawings

CHROMIUM-HISTIDINE COMPLEXES AS NUTRIENT SUPPLEMENTS

BACKGROUND OF THE INVENTION

1. Field of the Invention

Chromium, a physiologically important metal, is an essential element required for normal carbohydrate and lipid metabolism. Insufficient amounts may result in improper functioning of the metabolic process and lead to a number of physiological disorders. Membranes of the absorptive cells of the mammalian intestine often present a barrier to effective absorption of chromium, leading to insufficient amounts present in the bloodstream. The present invention relates to a chromium complex having improved absorption capabilities.

2. Description of the Relevant Art

Normal dietary chromium intake for humans and other mammalians is often suboptimal. Insufficient dietary intake of chromium leads to increases in risk factors associated with diabetes and cardiovascular diseases including elevated circulating insulin, glucose, triglycerides, total cholesterol, reduced HDL-cholesterol and impaired immune function (Anderson, R. A. 1998. *J. Am. Coll. Nutr.* vol. 17, pp. 548–555).

The beneficial effects of supplemental chromium on human subjects have been reviewed by Anderson (supra). There are more than 30 studies reporting beneficial effects on subjects with varying degrees of glucose intolerance, ranging from marginally elevated to overt diabetes. Supplemental chromium has been shown to improve the signs and/or symptoms of diabetes in people with glucose intolerance [Cefalu et al. 1999. *J. Trace Elem. Exptl. Med.* (In press)] and type 1 (Ravina et al. 1995. *J. Trace Elem. Exptl. Med.* vol. 8, pp. 183–190), type 2 (Ravina et al., supra; Anderson et al. 1997. *Diabetes.* vol. 46, pp. 1786–1791), gestational [Jovanovic et al. 1999. *J. Trace Elem. Exptl. Med.* (In press)] and steroid-induced diabetes [Ravina et al. 1999. *Diabetes Med.* vol. 16, pp. 164–167; Ravina et al. 1999. *J. Trace Elem. Exptl. Med.* (In press)]. Chromium also improves insulin function by increasing insulin binding to cells, insulin receptor number and insulin receptor phosphorylation, leading to increased insulin sensitivity. The amounts of supplemental chromium shown to have beneficial effects in these studies ranged from 200 to 1000 $\mu$g per day. In the study of Anderson et al. (supra) involving 180 subjects with type 2 diabetes, chromium effects were greater at 1000 $\mu$g per day than at 200 $\mu$g per day. The most dramatic improvements were shown in hemoglobin $A_{1C}$, which is a reliable indicator of long-term glucose control. Hemoglobin $A_{1C}$ in the placebo group was 8.5±0.2%, 7.5±0.2% in the 200-$\mu$g group and 6.6±0.1% in the group of subjects receiving 1000 $\mu$g of chromium as chromium picolinate per day for 4 months. Improvements in women with gestational diabetes were also greater in the group receiving 8 $\mu$g per kg body weight per day compared with those receiving 4 $\mu$g per kg body weight (Jovanic et al., supra). Steroid-induced diabetes that could not be controlled by oral hypoglycemic medications and/or insulin was also improved to acceptable levels in 47 of 50 people given 600 $\mu$g of chromium as chromium picolinate per day for 2 weeks followed by a daily chromium maintenance dose of 200 $\mu$g (Ravina et al., *Diabetes Med.*, supra; Ravina et al., 1999, *J. Trace Elem. Exptl. Med*, supra). Insulin sensitivity of obese subjects with a family history of diabetes also improved following 1000 $\mu$g daily of supplemental chromium as chromium picolinate (Cefalu et al., supra).

Blood lipid levels have also been shown to improve following chromium supplementation, with the greatest improvements in total cholesterol, HDL-cholesterol and triglycerides in subjects with the highest initial levels.

It is thus clear that normal dietary intake of chromium is often suboptimal and that beneficial effects can be observed following supplementation. The most widely-used supplements are chromium picolinate and chromium polynicotinate. Chromium picolinate is currently the most widely used, but it is not water soluble, and questions concerning toxicity have been raised (Sterns et al. 1995. *FASEB J.* vol. 9, pp. 1643–1649). Chromium polynicotinate is a poorly-absorbed mixture of a number of compounds; it is not stable and likely forms insoluble olated chromium polymers. The absorption of chromium from chromium chloride is generally approximately 0.4% (Anderson et al. 1983. *J. Nutr.* vol. 113, pp. 308–311) and from chromium picolinate, currently the most common chromium supplement, approximately 1.2% at intakes up to 1000 $\mu$g per day (Campbell et al. 1999. *J. Appl. Physiol.* vol. 86, pp. 29–30). Chromium incorporation into rat tissues has been shown to vary widely depending upon form (Anderson et al. 1996. *J. Trace Elem. Exptl. Med.* vol. 9, pp. 11–25). The highest concentrations were found in the kidney, followed by liver, spleen, heart, lungs and gastrocnemius muscle. The remaining chromium compounds that are available commercially are largely untested regarding both biological activity and absorption. Additional forms of chromium with improved absorption are urgently needed to help prevent and/or alleviate signs, symptoms and other risk factors associated with diabetes and cardiovascular diseases.

SUMMARY OF THE INVENTION

We have discovered a new form of chromium containing the amino acid histidine, which has surprisingly better absorption than any available chromium-containing compound tested. The complex should pose little or no toxicity, other than that for chromium itself, which is very low. Histidine, an essential amino acid, would be beneficial even at levels several-fold higher than would be present in a nutritional supplement.

In accordance with this discovery, it is an object of the invention to provide a chromium-histidine complex useful as a nutritional supplement and having improved absorption capability over currently available chromium nutritional supplements.

It is also an object of the invention to provide a composition comprising the novel chromium-histidine complex and an ingestible carrier.

Other objects and advantages will become readily apparent from the following description.

DETAILED DESCRIPTION OF THE INVENTION

More than three decades ago chromium was found to be an essential nutrient when rats fed a Torula yeast-based diet developed impaired glucose tolerance that was reversed by an insulin potentiating factor whose active component was shown to be trivalent chromium (Mertz and Schwarz. 1959. *Am. J. Physiol.* vol. 196, pp. 614–618; Schwarz and Mertz. 1959. *Arch. Biochem. Biophys.* vol. 85, pp. 292–295). The element has subsequently been established as essential for fish, mice, squirrel monkeys, guinea pigs, pigs, cattle and humans (Anderson, supra). The nutritional requirement for chromium in humans was demonstrated during the 1970's when a patient on total parenteral nutrition developed severe signs of diabetes including weight loss, glucose intolerance and peripheral neuropathy that were refractory to insulin but improved by supplemental chromium (Jeejeebhoy et al. 1977. *Am. J. Clin. Nutr.* vol. 30, pp. 531–538).

Although chromium as a dietary supplement has been available for some time, problems of administration have persisted apparently due to a lack of absorption in the gastrointestinal tract. Without adequate absorption, the element cannot be distributed to those sites in the body which would effectively utilize it.

Amino acid-chromium complexes using other amino acids had previously been disclosed (Abdel-Monem, U.S. Pat. No. 3,925,433, Dec. 9, 1975; Ashmead et al., U.S. Pat. No. 4,863,989, Sep. 5, 1989; Ridenour, U.S. Pat. No. 5,702,718, Dec. 30, 1997; Ashmead et al., U.S. Pat. No. 5,614,553, Mar. 25, 1997; Anderson et al., 1996, supra), however, none had studied the relative effectiveness of chromium-histidine complexes in human absorption. Experiments were carried out to investigate the efficacy of chromium-histidine complexes in the absorption process. Chromium was administered in the formulations listed in Table 1 at dosages of 200 $\mu$g chromium to three adult males and three females, and absorption during the first 24 hours was measured based on urinary chromium excretion. Results are shown in Table 1 where it can be seen that the novel chromium-histidine complex is absorbed at almost twice the level as that of the closest sample, chromium picolinate.

The complex may be prepared as described in Example 1. Complexation results in at least two histidine residues attached to the chromium metal ion, providing a multi-ringed structure. Bonds may be formed between the metal ion and both the carboxyl and amino groups of the amino acid. It is believed that, since histidine contains three nitrogens (as electron donors) as well as a ring component, the possibility of the formation of a number of heterocyclic rings exists, thus forming a multiplex unit.

TABLE 1

Absorption of Chromium Compounds.

| COMPOUND | $\mu$GRAMS ABSORBED |
| --- | --- |
| Control | 0.07 ± 0.02[a] |
| Chromium polynicotinate | 0.17 ± 0.04[a] |
| Chromium glycine, cysteine, glutamic acid, nicotinic acid | 0.24 ± 0.06[a] |
| Chromium pidolate | 0.42 ± 0.07[b] |
| Chromium chloride | 0.44 ± 0.07[b] |
| Chromium methionine | 0.78 ± 0.13[c] |
| Chromium picolinate | 1.81 ± 0.29[d] |
| Chromium histidine | 3.1 ± 0.32[e] |

Chromium absorbed the first 24 hours following intake of 200 $\mu$g of chromium in the various complexes listed, based on urinary chromium excretion (3 adult males and 3 females).
[a, b, c, d, e]Numbers with different superscripts are significantly different at p < 0.05 using Duncan's Multiple Range Test (SAS Institute, Cary, NC).

Chromium-histidine compounds may be used for, but are not limited to, improvements in glucose, insulin, cholesterol, HDL-cholesterol, triglycerides and other risks factors associated with diabetes and cardiovascular diseases. These Compounds may also improve muscle mass and decrease body fat. Supplements should be of benefit to humans as well as other mammals such as farm animals and pets.

The Estimated Safe and Adequate Daily Dietary Intake (ESADDI) for chromium for children 7 years to adult is 50 to 200 $\mu$g per day (National Research Council, Recommended Dietary Allowance, 10th ed., Washington, D.C.: National Academy Press, 1989). Normal dietary intake of chromium for adults is suboptimal based upon the recommended intakes and studies showing beneficial effects of supplemental chromium. Normal dietary intake of people in the U.S. is approximately 50 to 60% of the minimum suggested minimum daily intake of about 50 $\mu$g (Anderson et al. 1991. In *Seventh International Symposium on Trace Elements in Man and Animals*. Momcilovic, B., ed. Dubrovnik, pp. 3–6).

Chromium-histidine complexes may be combined with any ingestible carrier for consumption as a tablet, capsule or as a fortificant in foods or food products. Since the complex is water-soluble and stable in aqueous solutions, various aqueous solutions may also be effectively utilized. Acceptable carriers are well-known in the art, and these products may be prepared according to processes well-known to those of skill in the art. As a chromium supplement for humans, capsules, tablets or their equivalent containing about 100 to about 200 $\mu$g of chromium should be consumed once or twice daily between meals. Maximal beneficial effects of chromium are anticipated to occur at about 400 $\mu$g of chromium as chromium-histidine complex per day or less. It should be noted that, since chromium is the essential nutrient of interest, effective amounts are given in terms of chromium per se rather than in terms of the total complex.

EXAMPLES

Example 1

Synthesis of Histidine Complexes

Three-fold molar excess of histidine is added slowly to chromic acetate or chromic chloride in an aqueous solution at 80° C. The solution is then heated an additional 30 min, cooled to approximately room temperature, and the pH adjusted to pH 5 to 5.5 with concentrated ammonium hydroxide. After cooling, sample can be freeze-dried and used as a nutrient supplement. Other amino acids may also be included in the formulation, but at least one molar equivalent of histidine per mole of chromium must be present.

We claim:

1. A composition useful as a nutritional supplement comprising a chromium-histidine complex in an amount effective for improving the absorption of chromium in mammals and an ingestible carrier.

2. The composition of claim 1, wherein said effective amount of chromium-histidine is from about 50 $\mu$g to about 1000 $\mu$g of chromium.

3. The composition of claim 2, wherein said effective amount of chromium-histidine is from about 100 $\mu$g to about 400 $\mu$g of chromium.

4. The composition of claim 3, wherein said effective amount of chromium-histidine is from about 100 $\mu$g to about 200 $\mu$g of chromium.

5. The composition of claim 4, wherein said composition is in the form of a tablet, a capsule, an aqueous solution, a food or a food product.

* * * * *